United States Patent [19]

Abatjoglou

[11] 4,278,517

[45] Jul. 14, 1981

[54] OSMIUM CATALYZED HYDROXYLATION OF OLEFINS WITH SELENOXIDE COOXIDANTS

[75] Inventor: Anthony G. Abatjoglou, Charleston, W. Va.

[73] Assignee: Union Carbide Corporation, New York, N.Y.

[21] Appl. No.: 163,313

[22] Filed: Jun. 26, 1980

[51] Int. Cl.$^3$ .................. B01J 19/12; C07C 31/20; C07C 31/27
[52] U.S. Cl. .................. 204/158 R; 260/464; 260/465.6; 260/550; 562/587; 568/579; 568/623; 568/833; 568/847; 568/860
[58] Field of Search ............ 568/860, 833, 579, 623, 568/847; 204/158 R; 562/587; 260/464, 465.6, 550

[56] References Cited

U.S. PATENT DOCUMENTS

| | | | |
|---|---|---|---|
| 2,754,325 | 7/1956 | Smith | 568/860 |
| 2,773,101 | 12/1956 | Smith et al. | 568/860 |
| 3,317,592 | 5/1967 | Maclean et al. | 568/860 |
| 3,427,348 | 2/1969 | Olson | 568/860 |
| 3,488,394 | 1/1970 | Cummins | 568/833 |
| 3,642,909 | 2/1972 | Priestly | 260/550 |
| 3,846,478 | 11/1974 | Cummins | 568/860 |
| 3,928,473 | 12/1975 | Shalit | 568/860 |
| 4,008,136 | 2/1977 | Williams | 204/158 R |
| 4,049,724 | 9/1977 | Sheng et al. | 568/860 |

*Primary Examiner*—Joseph E. Evans
*Attorney, Agent, or Firm*—Bernard Lieberman

[57] ABSTRACT

A process for producing glycols by the catalytic oxidation of olefinic compounds which comprises contacting an olefinic compound with an organic selenoxide in an aqueous alkaline medium in the presence of a catalytic amount of octavalent osmium to form the corresponding glycol.

9 Claims, No Drawings

OSMIUM CATALYZED HYDROXYLATION OF OLEFINS WITH SELENOXIDE COOXIDANTS

This invention relates to the oxidation of olefinic compounds to form the corresponding glycols, and more particularly, to the oxidation of such olefinic compounds in the presence of an organic selenoxide and a catalytic amount of octavalent osmium.

The formation of glycols from olefins wherein the olefinic compound is catalytically oxidized in the presence of osmium tetroxide and a stoichiometric cooxidant is well known in the art. Among the known cooxidants for this process are hydrogen peroxide, metal chlorates and teritary butyl hydroperoxide. Thus, for example, the use of silver chlorate as a cooxidant in an osmium tetroxide catalyzed reacton to form glycol is disclosed in Hofmann, Ber. 45, p. 3329 (1912); U.S. Pat. No. 2,437,648 to Milas discloses hydrogen peroxide as a cooxidant for the abovedescribed reaction, while Van Rheenen et al, Tetrahedron Letters p. 1973 (1976) and U.S. Pat. No. 4,049,724 disclose, respectively, N-methyl-morpholine N-oxide and organic hydroperoxides as cooxidants for glycol formation. The use of oxygen as a stoichiometric cooxidant in the osmium catalyzed dihydroxylation of olefins has also been disclosed; see, for example, U.S. Pat. Nos. 3,317,592 and 3,928,473.

Processes using the aforementioned cooxidants to manufacture glycols from olefins have various disadvantages which, as a practical matter, limit their commercial utility. For example, those processes using hydrogen peroxide or silver chlorate as cooxidants are characterized by a variety of undesired byproducts formed by the overoxidation of the product glycol to ketols, and by the cleavage of carbon to carbon bonds. The use of N-methyl-morpholine as a cooxidant precludes the use of tri- and tetra-substituted olefins as process reactants due to the extremely low process efficiencies which are attendant thereto; and the use of t-butyl hydroperoxide as a cooxidant results in overoxidation of product glycols to ketols, and has the process disadvantages inherent with a non-regenerable cooxidant. Processes using oxygen as the cooxidant in the formation of glycols have the disadvantages of low reaction rates and rapid catalyst deactivation.

SUMMARY OF THE INVENTION

It has now been found that olefinic compounds can be catalytically oxidized to produce glycols by a process wherein an olefinic compound is contacted with an organic selenoxide in an aqueous alkaline medium in the presence of a catalytic amount of octavalent osmium to form the corresponding glycol. The invention is predicated on the discovery that the use of an organic selenoxide as a cooxidant allows the formation of glycols from olefins in the presence of a catalytic amount of octavalent osmium. The process of the invention avoids the problems which characterize the osmium tetroxide catalyzed reactions of the prior art, namely, the undesired formation of alphaketols by overoxidation of glycol product; the inability to use tri- and tetra-substituted olefins as process reactants; and the difficulty or inability to regenerate the cooxidant by a simple procedure, such as, by reaction with oxygen.

DETAILED DESCRIPTION OF THE INVENTION

The olefinic compounds which may be converted to glycols in accordance with the invention include cyclic or non-cyclic olefinic hydrocarbons, and substituted olefinic compounds having substituents such as hydroxyl, halogen, cyano, nitro, alkoxy, oxo, carbonyl or carboxyl groups and the like. Ethylene and propylene are particularly useful in the process of the invention.

The osmium catalyst is osmium in its +8 valance state and preferably in a water-soluble form. These octavalent osmium catalysts are conveniently prepared by reacting osmium tetroxide with a base such as sodium hydroxide in aqueous soluton to produce the active perosmate, i.e., the octavalent salt. The concentration of osmium in the aqueous solution is not critical and may vary from 1 part per million to 1 percent or more. A concentration of from 100 ppm to 2,000 ppm in the aqueous solution is generally preferred.

The organic selenoxide used in the process of the invention is represented by the formula $R_1R_2SeO$, wherein $R_1$ and $R_2$ may comprise any organic substituent subject to the limitations of volatility and stability of such selenoxide. Thus, for example, a selenoxide where both $R_1$ and $R_2$ are methyl will generally be unduly volatile for convenient operation of the process. In a preferred embodiment of the process, the selenoxide is used in catalytic rather than stoichiometric amounts by oxidizing the reduced selenide to the corresponding selenoxide with photochemically generated singlet oxygen under the process conditions used for olefin oxidation to glycol. The preparation of singlet oxygen is well known in the art and is described, for example, in R. W. Denny et al, "Sensitized Photooxygenation Of Olefins", Organic Reactions, Vol. 20, p. 133, John Wiley and Sons, New York (1973). In accordance with the aforementioned preferred embodiment, the selenoxide selected for the process must be such as to form a selenide which can readily regenerate the selenoxide by reaction with oxygen. For purposes of stability and ease of reoxidation, the preferred selenoxides of the invention are selected from among diaryl selenoxides, aryl methyl selenoxides or mixtures thereof.

The reaction is carried out in the liquid phase in an aqueous alkaline solution. An organic cosolvent is generally added to the solution to achieve high solubility of the olefin in the liquid phase. Any water miscible organic solvent that is not oxidizable under the reaction conditions of the process is suitable for this purpose. Among the preferred organic cosolvents are acetone, acetonitrile, dimethylsulfoxide, sulfolane, dimethylformamide, hexamethylphosphoramide, and tert-butanol. The weight ratio of water to organic cosolvent may vary widely within the range of solubility of the components to form a homogeneous solution.

The pH of the aqueous solution is an important process variable. The initial pH of the solution should be above 7 to insure operation of the process in an alkaline medium. Alkalinity is required to reduce the volatility of the octavalent osmium catalyst in solution and to increase the rate of the reaction of olefin to glycol. The initial pH range of the solution may vary from 7.5 to 12 with a pH of from 8 to 10 being generally preferred. The various buffering agents which may be advantageously employed to provide the desired pH range in aqueous solutions are well known in the art.

The process may be carried out at temperatures ranging from ambient to about 100° C. or higher. The higher the temperature, the faster the rate of reaction. With normally gaseous olefins such as ethylene and propylene, elevated pressures are generally preferred to increase the solubility of the olefin in the liquid phase and thereby increase the rate of reaction. In general, however, the reaction pressure is not a critical process variable.

EXAMPLE 1

A 100 ml Fischer-Porter glass pressure reactor, equipped with a magnetic stirring bar was successively charged with 2.5 g (0.01 moles) of diphenylselenoxide, 10 ml acetone, 10 ml 0.1 N potassium carbonate solution, and 0.63 ml of an osmium tetroxide solution (4% $OsO_4$ in 0.1 N $K_2CO_3$). The reactor was attached to a gas manifold, flushed with nitrogen and then pressurized with 80 psig ethylene. The mixture was magnetically stirred at room temperature for two hours until the reaction of the gaseous olefin ceased as evidenced by a constant gas pressure. Sodium bisulfate (5 ml of a 10 wt. % aqueous solution) was added to reduce both the remaining selenoxide and osmium tetroxide. The reaction mixture was transferred to a separatory funnel and the oily layer of diphenylselenide, formed during reaction, separated from the aqueous layer containing the solvent and glycol product. The water-acetone layer contained 0.49 g ethylene glycol (80% yield based on the amount of diphenylselenoxide used) as determined by gas chromatographic analysis.

EXAMPLE 2

The purpose of this experiment was to demonstrate the use of a different selenoxide in the procedure of Example 1.

The procedure of Example 1 was followed except that 1.87 g (0.01 moles) of phenylmethylselenoxide was used in place of diphenylselenoxide. Ethylene glycol was formed in an amount of 0.47 g (77% yield based on the amount of phenylmethylselenoxide used), as determined by gas chromatographic analysis.

EXAMPLE 3

The purpose of this experiement was to demonstrate the use of a mono-substituted gaseous olefin as a reactant.

The procedure of Example 1 was followed except that propylene was used in place of ethylene. Propylene glycol in an amount of 0.72 g (95% yield based on the amount of diphenylselenoxide used) was formed as determined by gas chromatographic analysis.

EXAMPLE 4

The purpose of this experiment was to demonstrate the use of a disubstituted liquid olefin as a reactant.

A 100 ml round-bottom, three-neck flask, equipped with a magnetic stirring bar, thermometer, reflux condenser and dropping funnel, was charged successively with 5 g (0.02 moles) diphenylselenoxide, 20 ml acetone, 20 ml 0.1 N potassium carbonate solution and 1.3 ml of an osmium tetroxide solution (4% osmium tetroxide in 0.1 N potassium carbonate). Cyclohexene (2.1 g, 0.025 moles) was added at room temperature, and the mixture was stirred overnight. Sodium bisulfite (10ml of a 10 wt. % aqueous solution) was then added to reduce both the remaining selenoxide and the osmium tetroxide. The mixture was transferred to a separatory funnel where the layer of selenide separated from the aqueous layer. The water-acetone layer contained 1.47 g 1,2-cyclohexanediol (63% yield based on the amount of diphenylselenoxide used) as determined by gas chromatographic analysis.

To obtain the pure product, the water-acetone layer was extracted with three, 20 ml portions of chloroform and the combined extracts washed with two, 10 ml portions of water, and dried over 5 grams of anhydrous magnesium sulfate. The chloroform solution was then filtered and concentrated on a rotary evaporator under reduced pressure. A solid residue (1.56 g) remained containing the crude 1,2-cyclohexanediol. The pure product was obtained by recrystallization from diethyl ether and characterized by infrared and nuclear magnetic resonance spectroscopy.

EXAMPLE 5

The purpose of this experiment was to demonstrate the use of a trisubstituted olefin as a reactant.

The general procedure of Example 4 was followed with the following exceptions: 2.5 g diphenylselenoxide, 10 ml acetone, 10 ml 0.1 N potassium carbonate and 0.63 ml osmium tetroxide solution (4% osmium tetroxide in 0.1 N potassium carbonate) were used instead of the corresponding amounts of such materials specified in Example 4; and 1-methyl-1-cyclohexene (1.92 g, 0.02 mole) dissolved in 15 ml acetone was added at room temperature to the mixture rather than cyclohexene. The mixture was stirred overnight and then treated as described in Example 4. The resulting water-acetone layer contained 0.39 g 1-methyl-1,2-cyclohexanediol (30% yield based on the amount of diphenylselenoxide used) as determined by gas chromatographic analysis.

EXAMPLE 6

The purpose of this experiment was to demonstrate the use of a tetrasubstituted olefin as a reactant.

The general procedure of Example 5 was followed with the following exceptions: tetramethylethylene (2.7 g, 0.032 moles) dissolved in 5 ml acetone was added at 50° C. (rather than olefinic compound addition at room temperature as previous examples). The mixture was maintained at 50° C. and stirred overnight and thereafter treated as in Example 5. The resulting water-acetone layer contained 1.13 g of 2,3-dimethyl-2,3-butanediol (98% yield based on the amount of diphenylselenoxide used) as determined by gas chromatographic analysis.

EXAMPLE 7

The purpose of this experiment was to demonstrate the oxidation of cyclohexene wherein the selenoxide cooxidant is regenerated from selenide with photochemically generated singlet oxygen.

A 100 ml Fischer-Porter glass pressure reactor was charged with 0.171 g (0.001 moles) phenylmethylselenide, 5 mg Rose Bengal, 35 ml acetonitrile, 35 ml 0.1 potassium carbonate, and pressurized with 50 psig oxygen. The reactor was irradiated with two 200 watts incandescent light bulbs for 60 minutes. The oxygen was vented and 0.1 ml osmium tetroxide solution (4% $OsO_4$ in 0.1 N $K_2CO_3$) and 2 ml (0.02 moles) cyclohexene were added to the mixture. The reactor was repressurized with 50 psi of oxygen and irradiated with two 200 watt incandescent light bulbs. Oxygen was continuously consumed as evidenced by a pressure drop in the reactor and periodically replenished by repressurizing the reactor to 50 psig. The reaction was interrupted after 2.5 hours. 1,2-Cyclohexanediol (1.2 g) was formed as determined by gas chromatographic analysis.

What is claimed is:

1. A process for producing glycols by the catalytic oxidation of olefinic compounds which comprises contacting an olefinic compound with an organic selenoxide in an aqueous alkaline medium in the presence of a catalytic amount of octavalent osmium to form the corresponding glycol.

2. The process of claim 1 wherein said organic selenoxide is selected from the group consisting of a diaryl selenoxide, an aryl methyl selenoxide, and mixtures thereof.

3. The process of claim 1 wherein following its formation, said glycol is recovered from said aqueous medium.

4. The process of claim 1 wherein the initial pH of the aqueous medium is at least 7.5.

5. The process of claim 4 wherein said pH is from 8 to 10.

6. The process of claim 1 wherein said olefinic compound is ethylene.

7. The process of claim 1 wherein said olefinic compound is propylene.

8. The process of claim 1 wherein said organic selenoxide is present in catalytic amounts.

9. The process of claim 1 wherein the selenoxide is regenerated from the reduced selenide with photochemically generated singlet oxygen.

* * * * *